(12) United States Patent
Oleksandrov et al.

(10) Patent No.: US 11,426,731 B2
(45) Date of Patent: Aug. 30, 2022

(54) CARTRIDGE FOR DIGITAL REAL-TIME PCR

(71) Applicant: OPTOLANE Technologies Inc., Seongnam-shi (KR)

(72) Inventors: Sergiy Oleksandrov, Sunwon-shi (KR); Do Young Lee, Seoul (KR); Min Sik Song, Daejon-shi (KR); Kyung Hak Choi, Yongin-shi (KR)

(73) Assignee: OPTOLANE TECHNOLOGIES INC., Seongnam-shi (KR)

( * ) Notice: Subject to any disclaimer, the term of this patent is extended or adjusted under 35 U.S.C. 154(b) by 91 days.

(21) Appl. No.: 16/390,380

(22) Filed: Apr. 22, 2019

(65) Prior Publication Data

US 2019/0329254 A1    Oct. 31, 2019

(30) Foreign Application Priority Data

Apr. 25, 2018  (KR) .................. 10-2018-0047632
Mar. 26, 2019  (KR) .................. 10-2019-0034671

(51) Int. Cl.
*B01L 3/00* (2006.01)
*C12Q 1/6806* (2018.01)
*C12Q 1/686* (2018.01)

(52) U.S. Cl.
CPC ... *B01L 3/502746* (2013.01); *B01L 3/502723* (2013.01); *C12Q 1/6806* (2013.01); *C12Q 1/686* (2013.01)

(58) Field of Classification Search
CPC ......... B01L 3/502715; B01L 3/502723; B01L 3/502746; B01L 7/52; B01L 2200/12;
(Continued)

(56) References Cited

U.S. PATENT DOCUMENTS 8,315,817 B2 * 11/2012 Kain et al. ........... C12Q 1/6874
                                                       702/20
2004/0132059 A1 * 7/2004 Scurati .............. B01L 3/502715
                                                       435/6.18
(Continued)

FOREIGN PATENT DOCUMENTS

CN  101297189 A  10/2008
CN  101928663 A  12/2010
(Continued)

*Primary Examiner* — Gautam Prakash
(74) *Attorney, Agent, or Firm* — Kile Park Reed & Houtteman PLLC

(57) ABSTRACT

A cartridge for digital real-time Polymerase chain reaction (PCR) includes a microfluidic chamber, a well array, a CMOS photo sensor array and a PCB. The microfluidic chamber includes an inlet formed for injection of a liquid sample, the microfluidic chamber being capable of injection molding. The well array includes a plurality of microwells through which upper and lower portions are perforated and being attached to a lower surface of the microfluidic chamber. The CMOS photo sensor array is disposed below the well array to capture a response image of a sample filled in microwells of the well array. The PCB has a vent formed for vacuum processing of micro flow path formed in the microfluidic chamber, a space formed between the well array and the microfluidic chamber, and a microwell formed in the well array as the liquid sample is injected through the inlet.

14 Claims, 23 Drawing Sheets

(58) Field of Classification Search
CPC ..... B01L 2200/0684; B01L 2200/0668; B01L
2200/0689; B01L 2200/0816; B01L
2200/0893; B01L 2300/123; B01L
2300/161; B01L 2300/0627; B01L
2300/0864; B01L 2400/049; C12Q
1/6806; C12Q 1/686; C12M 1/34; C40B
30/04; C40B 50/14; C40B 60/12; G01N
15/1463; G01N 21/64; G01N 21/6452;
G01N 2015/1465
See application file for complete search history.

(56) References Cited

U.S. PATENT DOCUMENTS

| | | | |
|---|---|---|---|
| 2006/0020371 A1* | 1/2006 | Ham | G01N 24/08 |
| | | | 700/266 |
| 2007/0003448 A1* | 1/2007 | Kanigan | B01L 3/563 |
| | | | 422/400 |
| 2011/0190146 A1* | 8/2011 | Boehm | B01L 3/502784 |
| | | | 506/7 |
| 2012/0196767 A1 | 8/2012 | Cooney et al. | |
| 2013/0052649 A1* | 2/2013 | Lee | B01L 3/5085 |
| | | | 435/6.12 |
| 2014/0038193 A1 | 2/2014 | Spoto et al. | |
| 2016/0339427 A1 | 11/2016 | Wiktor | |
| 2018/0221877 A1* | 8/2018 | Goto | B01L 3/502715 |

FOREIGN PATENT DOCUMENTS

| | | | | |
|---|---|---|---|---|
| CN | 102121054 A | 7/2011 | | |
| CN | 102277294 A | 12/2011 | | |
| CN | 103952482 A | 7/2014 | | |
| CN | 105543064 A | 5/2016 | | |
| CN | 105682802 A | 6/2016 | | |
| CN | 106459869 A | 2/2017 | | |
| CN | 107262170 A | 10/2017 | | |
| CN | 110358681 A | 10/2019 | | |
| DE | 102015001998 B3 | 2/2016 | | |
| JP | 2017-227646 | 12/2017 | | |
| TW | 201219770 A | 5/2012 | | |
| WO | WO-2015074076 A1 * | 5/2015 | ............ | B01L 3/0293 |
| WO | 2017/061600 | 4/2017 | | |

* cited by examiner

Air is pumped out

Air is pumped out

Air is pumped out

CARTRIDGE FOR DIGITAL REAL-TIME PCR

CROSS-REFERENCE TO RELATED APPLICATIONS

This application claims priority under 35 U.S.C. § 119 to Korean Patent Application No. 10-2018-0047632, filed on Apr. 25, 2018, and Korean Patent Application No. 10-2019-0034671, filed on Mar. 26, 2019 in the Korean Intellectual Property Office (KIPO), the contents of which are herein incorporated by reference in their entirety.

BACKGROUND OF THE INVENTION

Technical Field

Exemplary embodiments of the present invention relate to a cartridge for digital real-time Polymerase chain reaction (PCR). More particularly, exemplary embodiments of the present invention relate to a cartridge for digital real-time PCR capable of measuring the real-time reaction that can be performed at the same time while preventing an occurrence of air pockets at corners or edge regions of the reaction space.

Discussion of the Related Art

Gene amplification technology is a technology for repeatedly replicating and amplifying a specific base sequence of a small amount of deoxyribonucleic acid (DNA) or ribonucleic acid (RNA) in a sample. A typical gene amplification technique is a Polymerase chain reaction (PCR). Polymerase chain reaction (PCR) consists of DNA denaturation, primer annealing and primer extension. Since each step depends on the temperature of the sample, DNA can be amplified by changing the temperature of the sample repeatedly.

Polymerase chain reaction (PCR) is a method of amplifying a target DNA sequence. Previously, PCR has been generally performed in 96- or 384-well microplates. If higher throughputs are desired, conventional PCR methods in microplates are not cost effective or efficient. On the other hand, reducing the PCR reaction volumes lowers the consumption of reagents and may decrease amplification times from the reduced thermal mass of the reaction volumes. This strategy may be implemented in an array format (m×n), resulting in a large number of smaller reaction volumes. Furthermore, using an array allows for a scalable high throughput analysis with increased quantification sensitivity, dynamic range, and specificity.

Array formats have also been used to perform Digital real-time Polymerase chain reaction (dPCR). Results from dPCR can be used to detect and quantify the concentration of rare alleles, to provide absolute quantitation of nucleic acid samples, and to measure low fold-changes in nucleic acid concentration. Generally, increasing the number of replicates increases the accuracy and reproducibility of dPCR results.

The array format in most quantitative Polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

In dPCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal.

In the case of a digital real-time PCR, since the size of the reaction space is very small and the number thereof is very large, it is difficult to inject the sample into each of the reaction spaces.

Moreover, samples are not injected into corners or edge regions of the reaction space, so that air pockets may be formed at the corners or edge regions of the reaction space. When the air pockets expand or shrink due to temperature changes during the PCR process, error may occur in the test results.

In the conventional dPCR method, end-point PCR is used in which a sample is introduced into a reaction space and a nucleotide sequence is amplified. Therefore, it is impossible to measure the reaction in which the nucleotide sequence is amplified in real time in each reaction space.

SUMMARY

Exemplary embodiments of the present invention provide a cartridge for digital real-time PCR capable of simultaneously real-time PCR measurement while preventing an occurrence of air pockets in corners and edge regions of the reaction space.

According to one aspect of the present invention, a cartridge for digital real-time Polymerase chain reaction (PCR) includes a microfluidic chamber, a well array, a CMOS photo sensor array and a PCB. The microfluidic chamber includes an inlet formed for injection of a liquid sample, the microfluidic chamber being capable of injection molding. The well array includes a plurality of microwells through which upper and lower portions are perforated and being attached to a lower surface of the microfluidic chamber. The CMOS photo sensor array is disposed below the well array to capture a response image of a sample filled in microwells of the well array. The PCB has a vent formed for vacuum processing of micro flow path formed in the microfluidic chamber, a space formed between the well array and the microfluidic chamber, and a microwell formed in the well array as the liquid sample is injected through the inlet.

In an exemplary embodiment of the present invention, the microfluidic chamber may include a base member and a square top plate member. The base member includes a first flat portion in a rectangular shape, a square support hole formed in a central region of the first flat portion, and a circular hole formed in an edge region of the first flat portion. The square top plate member includes a square flat second flat plate, a dish-shaped membrane switch, and a perforated inlet, and disposed on the base member.

In an exemplary embodiment of the present invention, the microfluidic chamber may include polydimethylsiloxane (PDMS) material.

In an exemplary embodiment of the present invention, the microfluidic chamber may have a low self-fluorescence.

In an exemplary embodiment of the present invention, the cartridge for digital real-time PCR may further include a sticker attached to the microfluidic chamber to form a bottom of micro flow path formed in the microfluidic chamber.

In an exemplary embodiment of the present invention, the well array may include an etched silicon material.

In an exemplary embodiment of the present invention, an upper surface of the CMOS photo sensor array is coated with a thin layer to form a bottom of the well after sealing.

In an exemplary embodiment of the present invention, the thin layer may include a PDMS material.

In an exemplary embodiment of the present invention, the well array may be coated in a hydrophilic.

In an exemplary embodiment of the present invention, the well array may be attached to the microfluidic chamber by plasma or thermal or UV curing adhesive.

In an exemplary embodiment of the present invention, the well array may have a thickness of less than 700 μm.

In an exemplary embodiment of the present invention, hexagonal microwells may be formed in the well array, and the pitch of the microwells is less than 150 μm.

In an exemplary embodiment of the present invention, the cartridge for digital real-time PCR may further include an upper case and a bottom case. The upper case is disposed above the microfluidic chamber and having a hole formed to correspond to the inlet. The bottom case is coupled to the bottom case to receive the microfluidic chamber, the well array, the CMOS photo sensor array, and the PCB, and having holes corresponding to the vent holes.

In an exemplary embodiment of the present invention, the cartridge for digital real-time PCR may further include a window member disposed over the membrane switch. In this case, the window member is arranged corresponding to a hole formed in a central region of the upper case.

In an exemplary embodiment of the present invention, the window member may include a transparent material.

In an exemplary embodiment of the present invention, the window member may include a PDMS material.

According to some exemplary embodiments of the present invention, it is possible to prevent a generation of air pockets in the corners or edge regions of the well array, which is a reaction space, when the PCR solution is moved through the pumping of the vacuum device and the solution fills the reaction space. Thus, it is possible to prevent an error caused by the air pocket from occurring in a result of a PCR test. Moreover, Real-time PCR reactions may also be measured since the well array is disposed on the CMOS photosensor array.

BRIEF DESCRIPTION OF THE DRAWINGS

The above and other features and aspects of the present invention will become more apparent by describing in detailed exemplary embodiments thereof with reference to the accompanying drawings, in which.

DETAILED DESCRIPTION OF THE INVENTION

Figure 1:
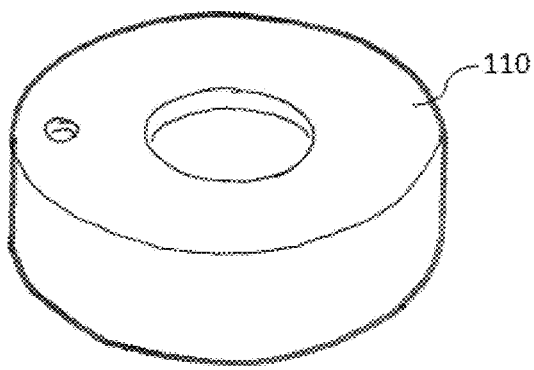
FIG. 1 is a perspective view schematically illustrating a digital real-time PCR cartridge according to an exemplary embodiment of the present invention.

The present invention is described more fully hereinafter with reference to the accompanying drawings, in which exemplary embodiments of the present invention are shown. The present invention may, however, be embodied in many different forms and should not be construed as limited to the exemplary embodiments set forth herein. Rather, these exemplary embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments of the invention are described herein with reference to cross-sectional illustrations that are schematic illustrations of idealized exemplary embodiments (and intermediate structures) of the present invention. As such, variations from the shapes of the illustrations as a result, for example, of manufacturing techniques and/or tolerances, are to be expected. Thus, exemplary embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

In various exemplary embodiments, the devices, instruments, systems, and methods for loading samples into an article used to detect targets in a large number of small volume samples. These targets may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule. In various exemplary embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation.

While generally applicable to quantitative Polymerase chain reactions (qPCR) where a large number of samples are being processed, it should be recognized that any suitable PCR method may be used in accordance with various exemplary embodiments described herein. Suitable PCR methods include, but are not limited to, digital real-time PCR, allele-specific PCR, asymmetric PCR, ligation-mediated PCR, multiplex PCR, nested PCR, qPCR, cast PCR, genome walking, and bridge PCR, for example.

As described below, according to various exemplary embodiments described herein, reaction sites may include, but are not limited to, through-holes, sample retainment regions, wells, indentations, spots, cavities, and reaction chambers, for example.

Various exemplary embodiments described herein are particularly suited for digital real-time PCR (dPCR). In digital real-time PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal.

In order to conduct a typical dPCR protocol, procedure, or experiment, it is advantageous to be able to divide an initial sample solution into tens of thousands or hundreds of thousands of test samples each having a volume of several nanoliters, at or about one nanoliter, or less than one nanoliter, in a way that is simple and cost effective. Because the number of target nucleotide sequences may be very small, it may also be important in such circumstances that the entire content of the initial solution be accounted for and contained in the plurality of reaction sites.

Exemplary embodiments described herein solve these and other dPCR design constraints by distributing an initial sample solution into a plurality of reaction sites in a way that accounts for all, or essentially all, of sample solution.

For high throughput PCR assays and dPCR methods, a strategy of using an array format to reduce reaction volumes of liquid sample while increasing the number of reactions performed at one time may be employed. The array of reaction volumes of liquid sample may be in a substrate in a plurality of reaction sites. Reaction sites may be, but are not limited to, through-holes, wells, indentations, spots, cavities, reaction chambers, or any structure that may hold a sample, according to various exemplary embodiments described herein. In some exemplary embodiments, the through-holes or wells may be tapered in diameter.

Reduction in reaction volumes of liquid sample may allow for a higher density of reaction volumes so that more reactions can be performed within a given area. For example, an array of reaction sites comprised of 300 µm diameter through-holes in a substrate may contain about 30 nL of reaction volume. By reducing the size of each through-hole in an array to 60-70 µm in diameter, for example, each reaction volume may be 100 pL of liquid sample. According to various exemplary embodiments described herein, reaction volumes may range from about 1 pL to 30 nL of liquid sample. In some exemplary embodiments, an array of reaction sites may be comprised of a variety of different volume reaction sites to increase dynamic range. Furthermore, dynamic range may be increased by using more than one dilution of the liquid sample.

Figure 2:
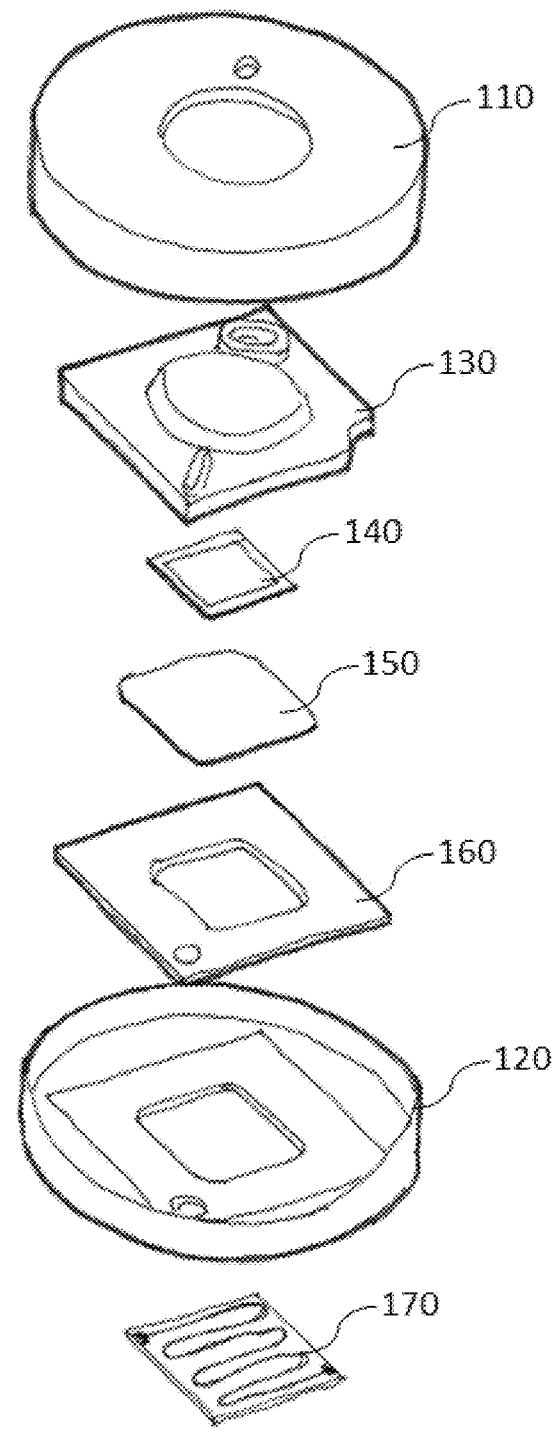
FIG. 2 is an exploded perspective view of the digital real-time PCR cartridge shown in FIG. 1.

FIG. 1 is a perspective view schematically illustrating a digital real-time PCR cartridge according to an exemplary embodiment of the present invention. FIG. 2 is an exploded perspective view of the digital real-time PCR cartridge shown in FIG. 1.

Referring to FIG. 1 and FIG. 2, a cartridge for digital real-time PCR according to an exemplary embodiment of the present invention includes an upper case 110, a bottom case 120, a microfluidic chamber 130, a well array 140, a CMOS (Complementary Metal-Oxide Semiconductor) image sensor 150 and a PCB 160 as an inspection module of a cartridge. In the present exemplary embodiment, the cartridge for digital real-time PCR may be detachably coupled to a reader system of digital real-time PCR equipment. In the present exemplary embodiment, the microfluidic chamber 130, the well array 140, the CMOS photo sensor array 150 and the PCB 160 may define a PCR module.

The upper case 110 includes a cover body of a donut shape including an upper hole formed in a central region and a window member disposed in the upper hole. The upper case 110 is coupled to the bottom case 120. In the present exemplary embodiment, the upper case 110 and the bottom case 120 have a flat cylindrical shape, but various shapes may be possible. The window member may include a transparent material. The window member may include polydimethylsiloxane (PDMS) material.

The bottom case 120 receives the microfluidic chamber 130, the well array 140, the CMOS photo sensor array 150 and the PCB 160 to be coupled to the upper case 110. The bottom case 120 and the upper case 110 may be coupled in a hook manner.

The microfluidic chamber 130 includes a membrane switch protruding upward, and an inlet formed on one side of the membrane switch for injecting a liquid sample. A lower edge region of the microfluidic chamber 130 is in contact with the edge region of the PCB 160. A recessed space is formed in a lower central region of the silicon chamber 130 to accommodate the CMOS photo sensor array 150 and the well array 140 mounted on the PCB 160. A space of a retreated shape is formed to accommodate the well array 140. The microfluidic chamber 130 may be formed of a material such as PDMS. The microfluidic chamber 130 has flexibility, transparency, PCR compatibility, and low autofluorescence. The microfluidic chamber 130 is capable of injection molding.

The well array 140 is attached to a lower surface of the microfluidic chamber 130 and is disposed on the CMOS photo sensor array 150. The well array 140 may be formed of an etched silicon material. The well array 140 includes a plurality of microwells (approximately 1,000~100,000) that perform as PCR reaction sites.

Figure 3:
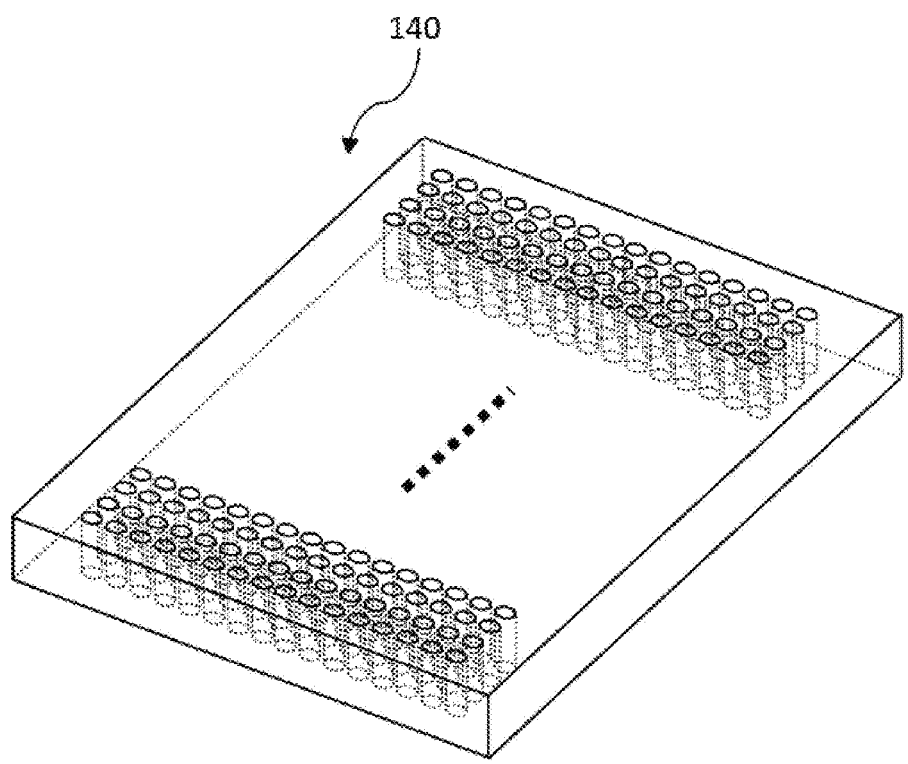
FIG. 3 is a perspective view schematically illustrating an example of a well array shape.
Figure 4A:
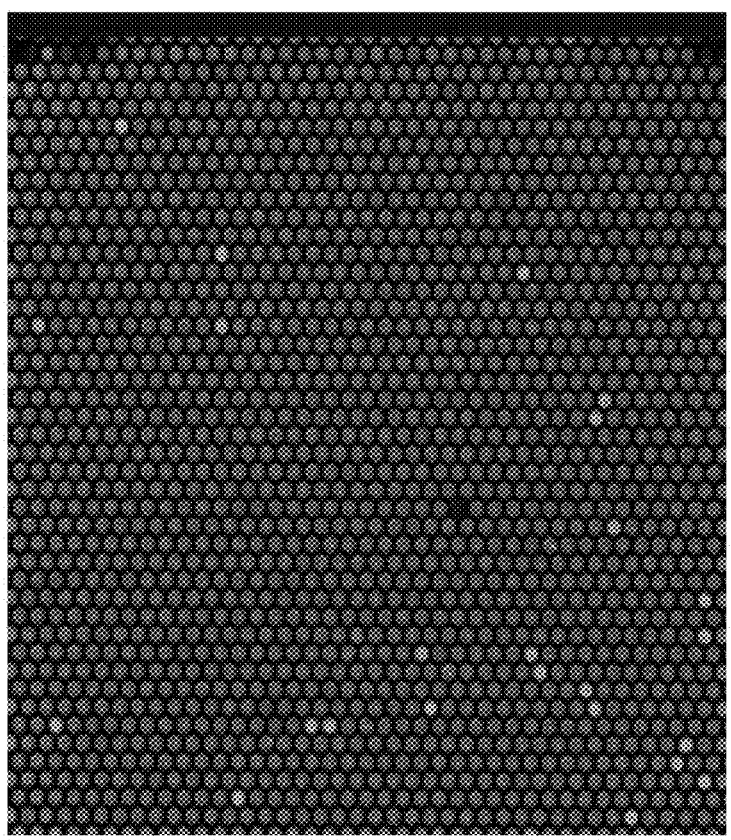
FIG. 4A and FIG. 4B are diagrams showing digital real-time PCR results.
Figure 4B:
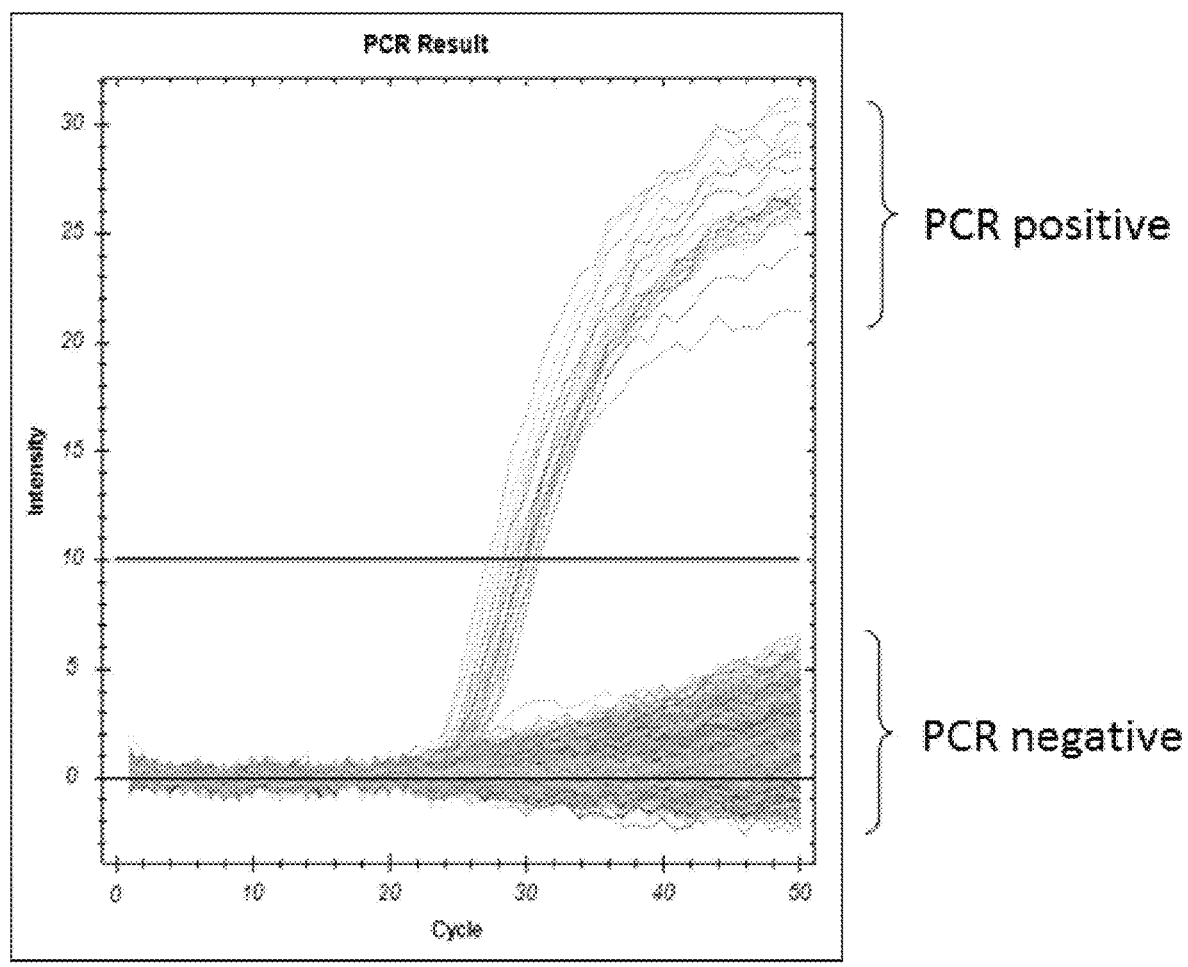

FIG. 3 is a perspective view schematically illustrating an example of a well array shape. FIG. 4A and FIG. 4B are diagrams showing digital real-time PCR results.

Referring to FIG. 3, a shape, size and volume of the microwells may be adjusted. The microwells have a shape in which upper and lower portions penetrate. In the present exemplary embodiment, the microwell may have a thickness of less than 700 µm and a pitch of less than 150 µm. The microwell may have various shapes such as a hexagonal shape, a circular shape, and the like. A hydrophilic coating layer may be formed on the well array 140. The well array 140 may be attached to the microfluidic chamber 130 by plasma, thermal or UV curable adhesives.

Referring again to FIG. 1 and FIG. 2, he CMOS photo sensor array 150 is disposed below the well array 140 to capture the PCR reaction products in the microwells of the well array 140 in real time. Particularly, the CMOS photo sensor array 150 is disposed to correspond to a substrate hole formed in the PCB 160, and receives lights emitted from the well array 140 to measure a PCR reaction product performed in the PCR device as shown in FIG. 4A. The measured PCR reaction product may be analyzed in the manner of a graph or the like, as shown in FIG. 4B.

FIG. 4A and FIG. 4B are diagrams showing digital real-time PCR results. In particular, FIG. 4A is a photograph showing PCR positive/negative results in a well array, and FIG. 4B is a graph for determining fluorescence in real time in each microwell to determine whether the well is positive or negative.

Referring again to FIG. 1 and FIG. 2, the upper surface of the CMOS photo sensor array 150 may be coated with a thin layer of material such as PDMS to form a bottom of the microwell after sealing.

The PCB 160 receives the CMOS photo sensor array 150. A vent hole 152 for vacuum processing may be formed through the PCB 160 so that liquid samples injected through the inlet may be rapidly supplied to the well array 140. The vent hole 152 is connected to a space 154 between the CMOS photo sensor array 150 and the well array 140.

In the present exemplary embodiment, the cartridge for digital real-time PCR may further include a heater 170 for thermal cycling. As used herein, thermal cycling may include using a thermal cycle, isothermal amplification, thermal convention, infrared mediated thermal cycling, or helicase dependent amplification, for example. In some exemplary embodiments, the chip may be integrated with a built-in heating element. In various exemplary embodiments, the chip may be integrated with semiconductors.

Figure 5A:
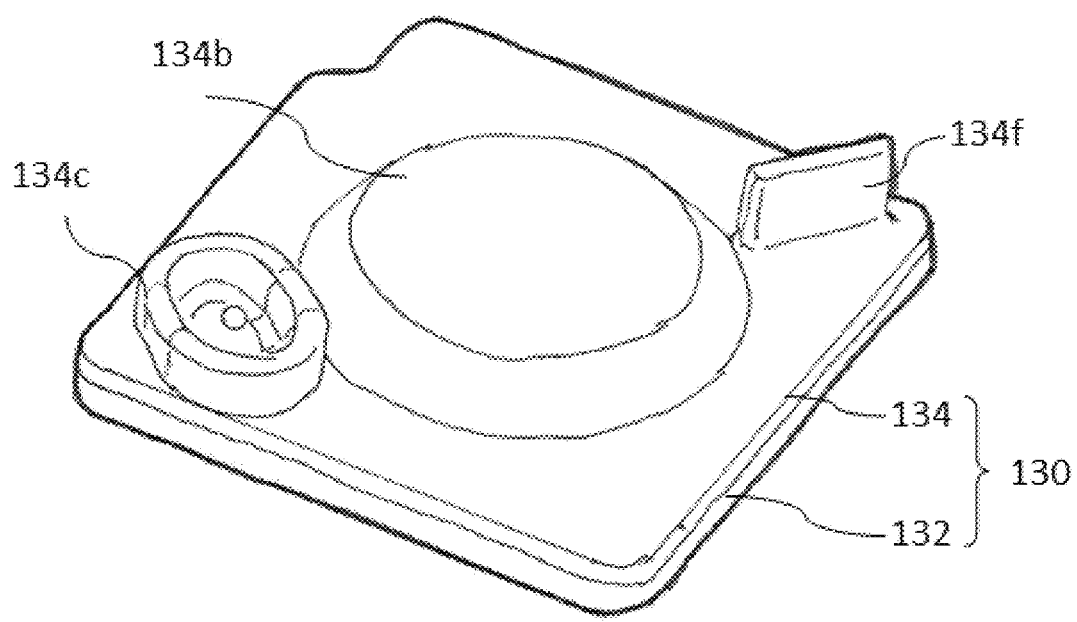
FIG. 5A is a front perspective view schematically explaining the microfluidic chamber shown in FIG. 2.
Figure 5B:
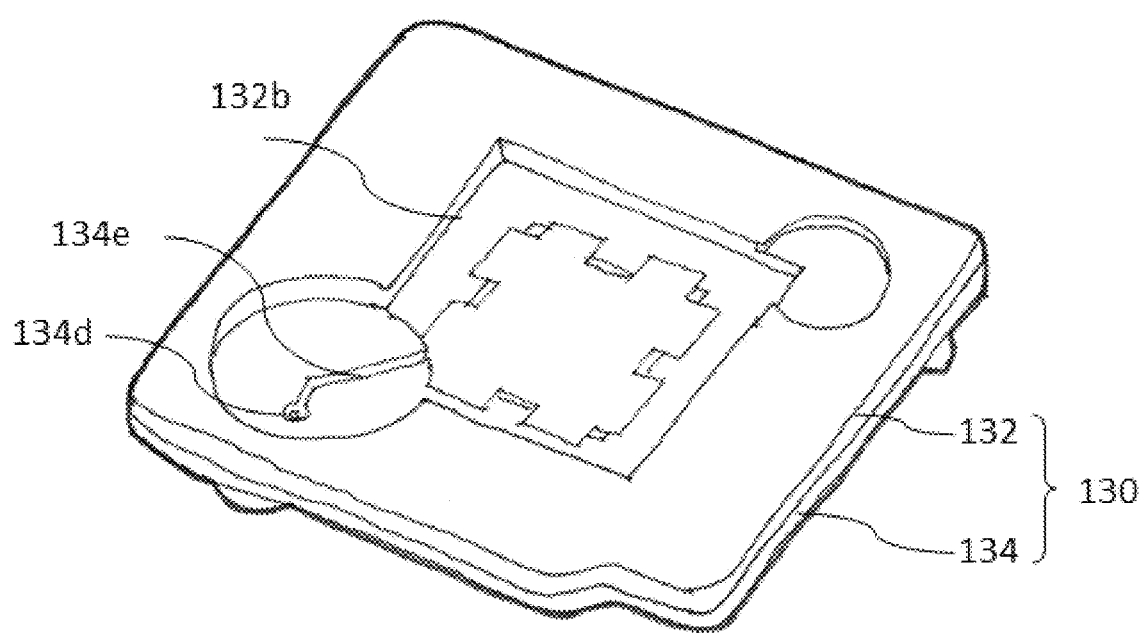
FIG. 5B is a rear perspective view schematically explaining the microfluidic chamber shown in FIG. 2.
Figure 5C:
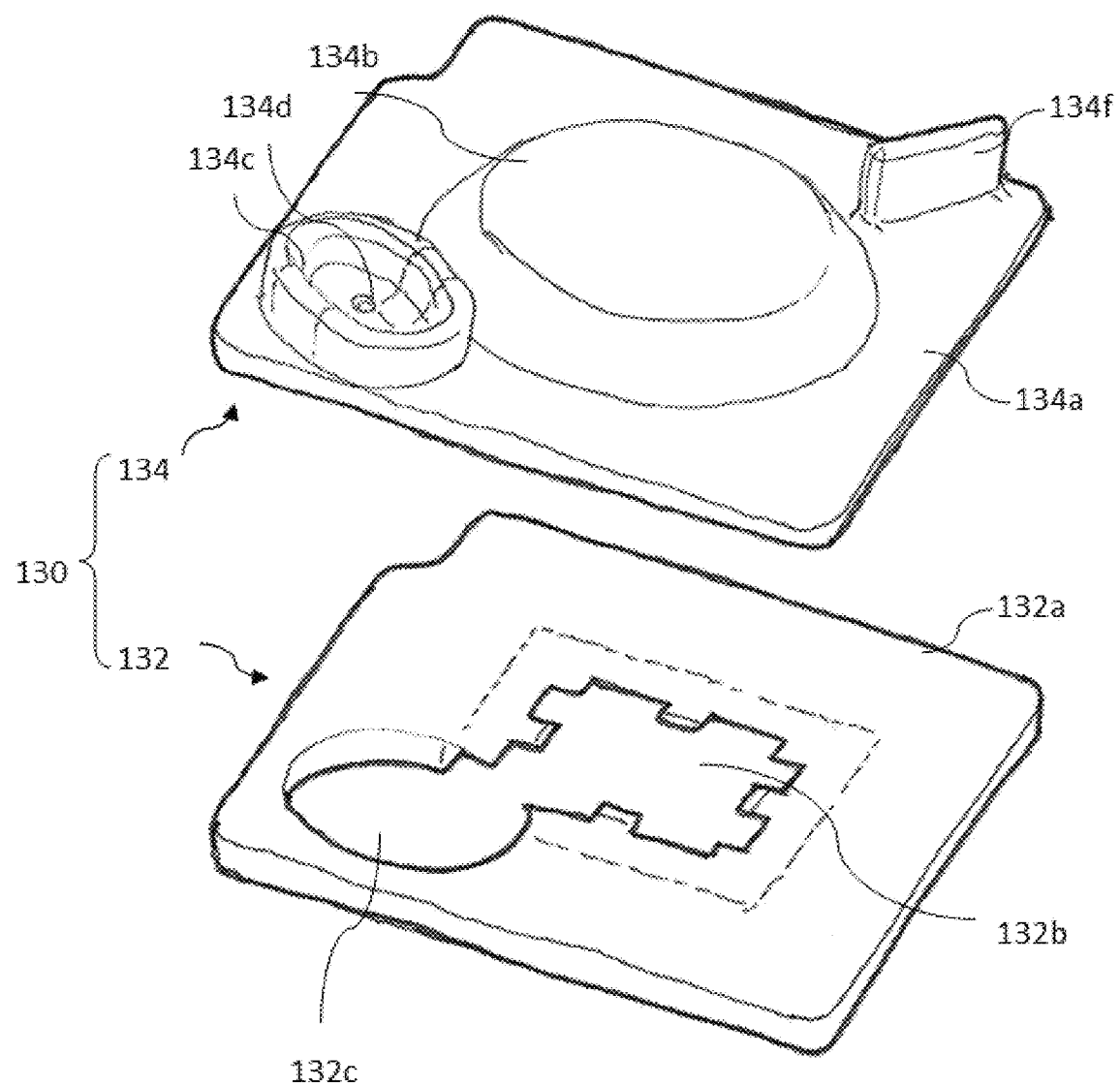
FIG. 5C is an exploded perspective view of the microfluidic chamber shown in FIG. 2.

FIG. 5A is a front perspective view schematically explaining the microfluidic chamber 130 shown in FIG. 2, FIG. 5B is a rear perspective view schematically explaining the microfluidic chamber 130 shown in FIG. 2, and FIG. 5C is an exploded perspective view of the microfluidic chamber 130.

Referring to FIG. 2 to FIG. 5C, the microfluidic chamber 130 according to the present exemplary embodiment includes a base member 132 of a rectangular shape and a top member 134 of a rectangular shape disposed on the base member 132. In the present exemplary embodiment, the base member 132 and the top member 134 are shown as being physically separated, but the base member 132 and the top member 134 may be integrally formed.

The base member 132 includes a first flat portion 132a of a square shape, a support hole 132b of a rectangular shape formed in a central region of the first flat portion 132a, and a flat hole 132c of a circle shape formed in a corner region of the first flat portion 132a. Guide holes protruding toward a central region may be formed in the support hole 132b to define a rectangular saw tooth shape.

The top member 134 includes a second flat portion 134a of a rectangular shape, a membrane switch 134b of a dish shape, and an inlet portion 134c of a closed loop shape. The second flat portion 134a is in close contact with an upper surface of the first flat portion 132a. The membrane switch 134b is disposed in a central region of the second flat portion 134a and protrudes upward from an observer's viewpoint. A lower region of the membrane switch 134b corresponds to the support hole 132b of the base member 132. Accordingly, a recessed space is formed at a bottom of the microfluidic chamber 130. The CMOS photo sensor array 150 and the well array 140 may be accommodated in the recessed space.

The inlet portion 134c has a fence shape and protrudes upward at one side of the membrane switch 134b to prevent liquid samples from flowing out to an outside. An inlet 134d is formed in a central region of the inlet portion 134c along a direction perpendicular to the base member 132.

A micro flow path 134e is formed in a region connecting the inlet 134d of the inlet portion 134c and a bottom edge region of the membrane switch 134b. The liquid samples injected into the inlet 134d of the inlet portion 134c reaches the bottom edge region of the membrane switch 134b through the micro flow path 134e.

The top member 134 may further include a grip part 134f protruding upward from the other side of the membrane switch 134b. The grip part 134f is disposed to face the inlet portion 134c with respect to the membrane switch 134b. The height of the grip part 134f may be higher than the height of the inlet portion 134c. The height of the inlet portion 134c and the height of the membrane switch 134b are substantially equal to each other.

As described above, in the microfluidic chamber 130, the inlet 134d and the micro flow path 134e are connected to each other. When the liquid sample is introduced through the inlet 134d, the liquid sample falls through the micro flow path 134e into the space formed below the membrane switch 134b. Also, when the membrane switch 134b is depressed, the liquid sample may be fully charged into each of the microwells of the well array 140 exposed through the micro channel 134e.

Figure 6:
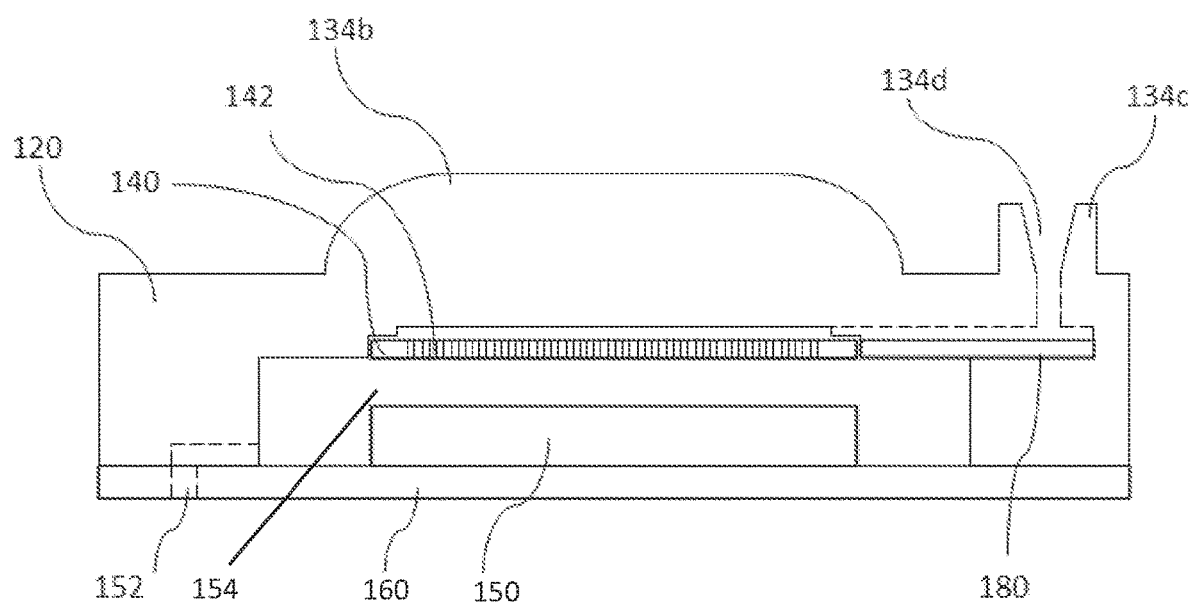
FIG. 6 is a cross-sectional view schematically illustrating the PCR module shown in FIG. 2.
Figure 7:
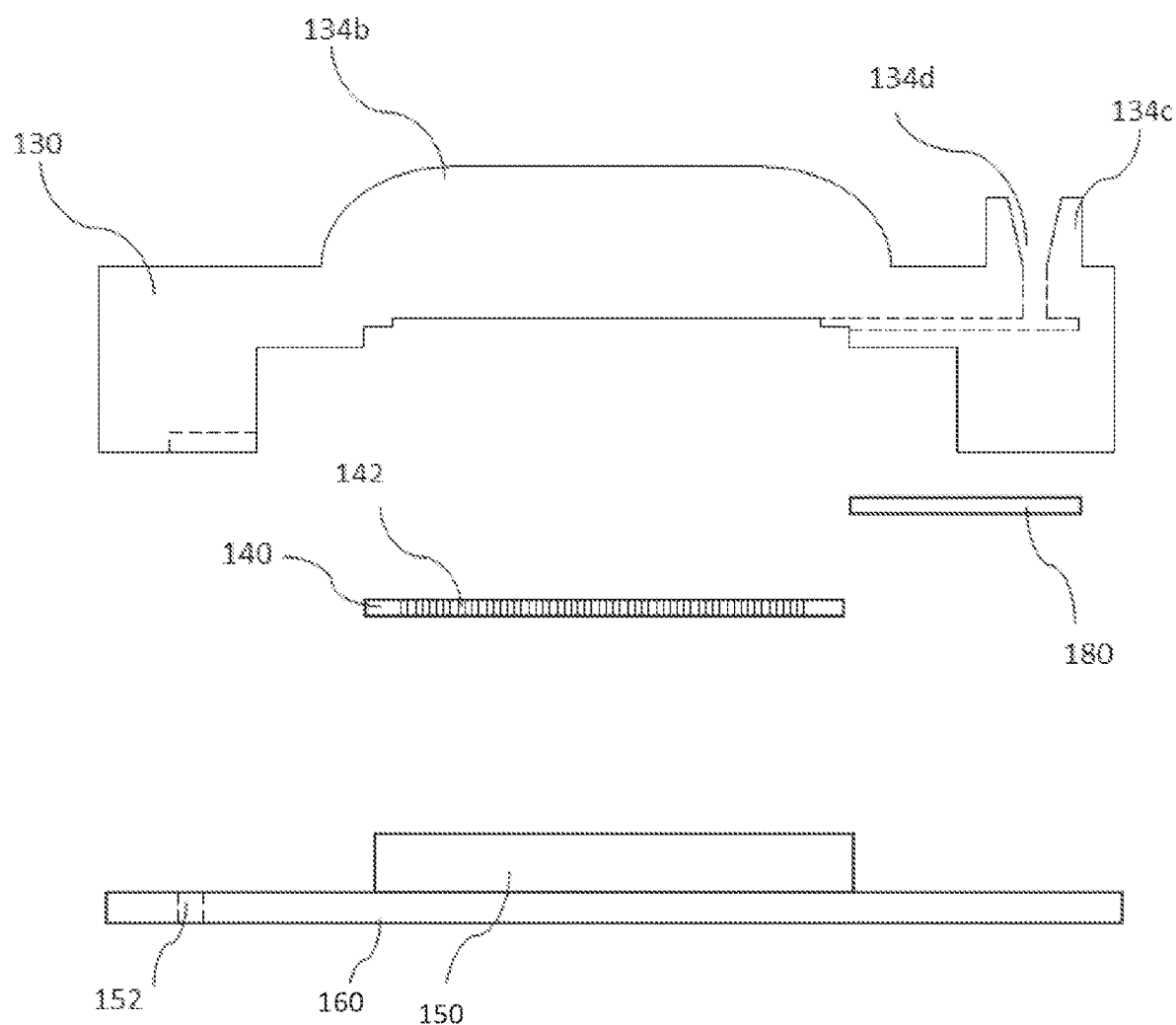
FIG. 7 is an exploded cross-sectional view schematically illustrating the PCR module shown in FIG. 6.

FIG. 6 is a cross-sectional view schematically illustrating the PCR module shown in FIG. 2. FIG. 7 is an exploded cross-sectional view schematically illustrating the PCR module shown in FIG. 6.

Referring to FIG. 2 to FIG. 7, a PCR module according to an exemplary embodiment of the present invention includes a microfluidic chamber 130, a well array 140, a CMOS photo sensor array 150, and a PCB 160.

A recessed space is formed in the bottom region of the microfluidic chamber 130 to receive the CMOS photo sensor array 150 and the well array 140 disposed on the PCB 160. Since the microfluidic chamber 130 has been described with reference to FIGS. 3A to 3C, a description thereof will be omitted.

The well array 140 is attached to the lower surface of the microfluidic chamber 130. The well array 140 is disposed on the CMOS photo sensor array 150 and inserted into a substrate hole formed in the PCB 160. The well array 140 includes a plurality of microwells 142. A shape, dimensions and number of the microwells 142 may be various. Each of the microwells 142 may contain an analytical sample such as a powder sample or a liquid sample. The analytical sample is a specific component for biological material analysis. That is, the analytical sample refers to a primer, a probe, an antibody, an aptamer, a DNA or an RNA polymerase, or the like, as a component for quantitative or qualitative analysis of a specific biological substance such as protein, DNA, RNA. In particular, the analytical sample refers to a component required for performing a real-time PCR, a canonical enzyme reaction, or an LCR (Ligase Chain Reaction).

The CMOS photo sensor array 150 is disposed below the well array 140 to capture an image of the PCR reaction product performed in the microwells 142 of the well array 140 in real time. The CMOS photo sensor array 150 is inserted into a substrate hole formed in the PCB 160. The CMOS photo sensor array 150 receives the emitted light and captures an image of the PCR reaction product performed in the PCR device. That is, the CMOS photo sensor array 150 detects an emission light generated from a plurality of probes by an excitation light beam. The detection of the emission light may be performed by a time division method or a wavelength division method.

In the case of the time division method, as the fluorescent material emits the emitted light in response to the excitation light, a fluorescent sensor array or a single sensor constituting an array detects the emission light passing through an emission filter, and detects the fluorescence by determining the time constant of the detected emitted light.

In the case of the above wavelength separation method, as the fluorescent material emits the emitted light in response to the excitation light, a fluorescent sensor array or a single sensor constituting an array detects the emission light passing through the emission filter, and detects the fluorescence through spectral analysis of the detected emitted light.

The PCB 160 is disposed below the microfluidic chamber 130 to receive the CMOS photo sensor array 150 mounted thereon. The PCB 160 is disposed in contact with the bottom edge region of the microfluidic chamber 130. A vent hole 152 is formed in a portion of the PCB 150 in contact with the bottom edge region of the microfluidic chamber 130. The vent hole 152 is connected to the space between the CMOS photo sensor array 150 and the well array 140.

When liquid samples are injected into the inlet 134d, air is pumped through a vacuum device (not shown) connected to the vent hole 152. As the air is pumped, the liquid samples injected into the inlet 134d flows into a portion of the well array 140, an upper region of the portion of the well array 140 and a lower region of the portion of the well array 140 via the micro channel 134e formed in the microfluidic chamber 130.

In the present exemplary embodiment, the PCR module may further include a sticker 180 that forms a bottom of the microchannel 134e formed in the microfluidic chamber 130. As the sticker 180 is attached to the microfluidic chamber 130, the liquid samples introduced into the micro flow path 134e may be supplied to the well array 140 without being leaked to other areas. The thickness of the sticker 180 and the thickness of the well array 140 may be substantially equal to each other.

In the present exemplary embodiment, the PCR module may further include an optical providing part (not shown) arranged to irradiate an excitation light towards a probe contained in each of the microwells 142 of the well array 140. In one exemplary embodiment, the light providing part may include a light source that emits light, such as a light emitting diode (LED) light source, a laser light source, or the like. The light emitted from the light source passes through or reflects the microwells 142 of the well array 140. In this case, the CMOS photo sensor array 150 may detect an optical signal generated by nucleic acid amplification.

In the present exemplary embodiment, the PCR module may further include a color filter (not shown) performing a function of selecting light having a predetermined wavelength. The color filter may be disposed on the CMOS photo sensor array 150.

Hereinafter, a method of using a digital real-time PCR cartridge according to an exemplary embodiment of the present invention will be described with reference to sequential drawings. For convenience of explanation, an illustration of the upper case 110 (shown in FIG. 2) and the bottom case 120 (shown in FIG. 2) is omitted.

Figure 8:
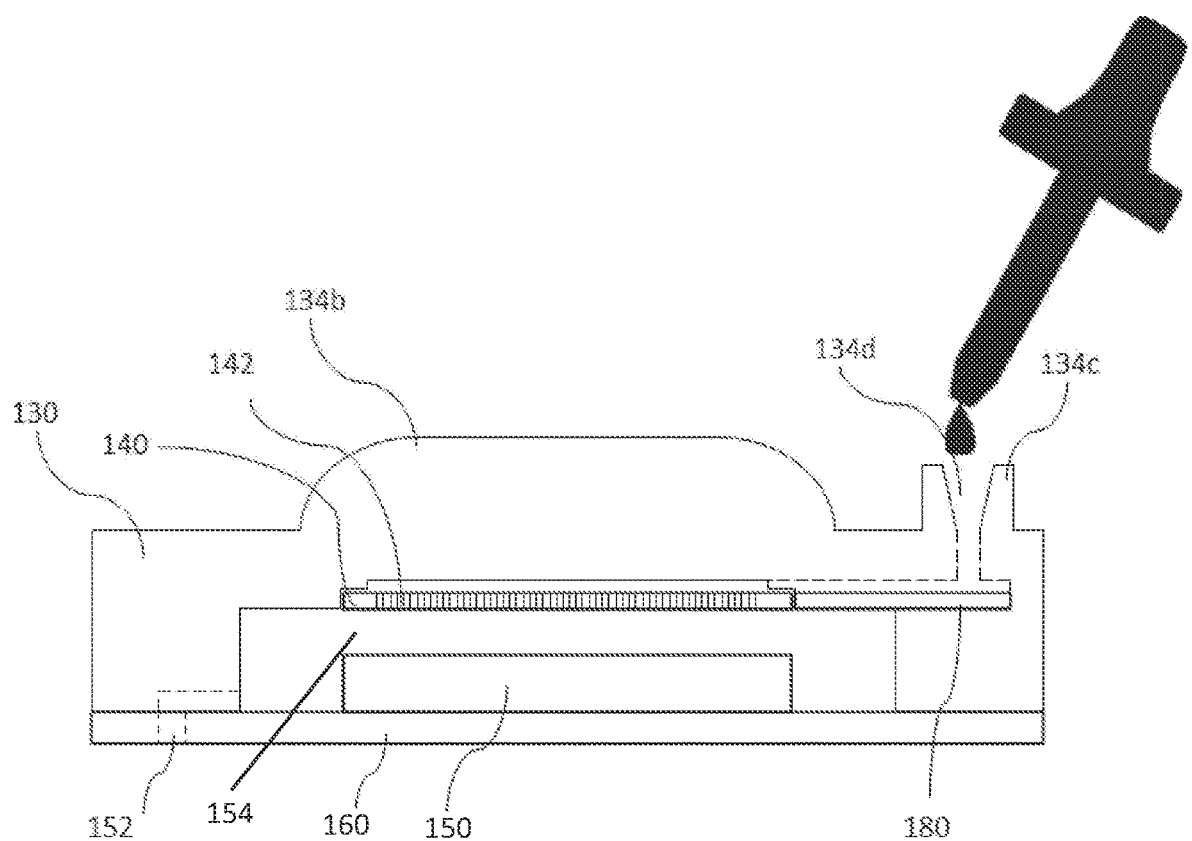
FIG. 8 is a cross-sectional view schematically explaining a first step of the PCR process using the PCR module shown in FIG. 6.

FIG. 8 is a cross-sectional view schematically explaining a first step of the PCR process using the PCR module shown in FIG. 6.

Referring to FIG. 8, as a first step of the PCR process, an empty PCR module is disposed on a flat position.

Figure 9:
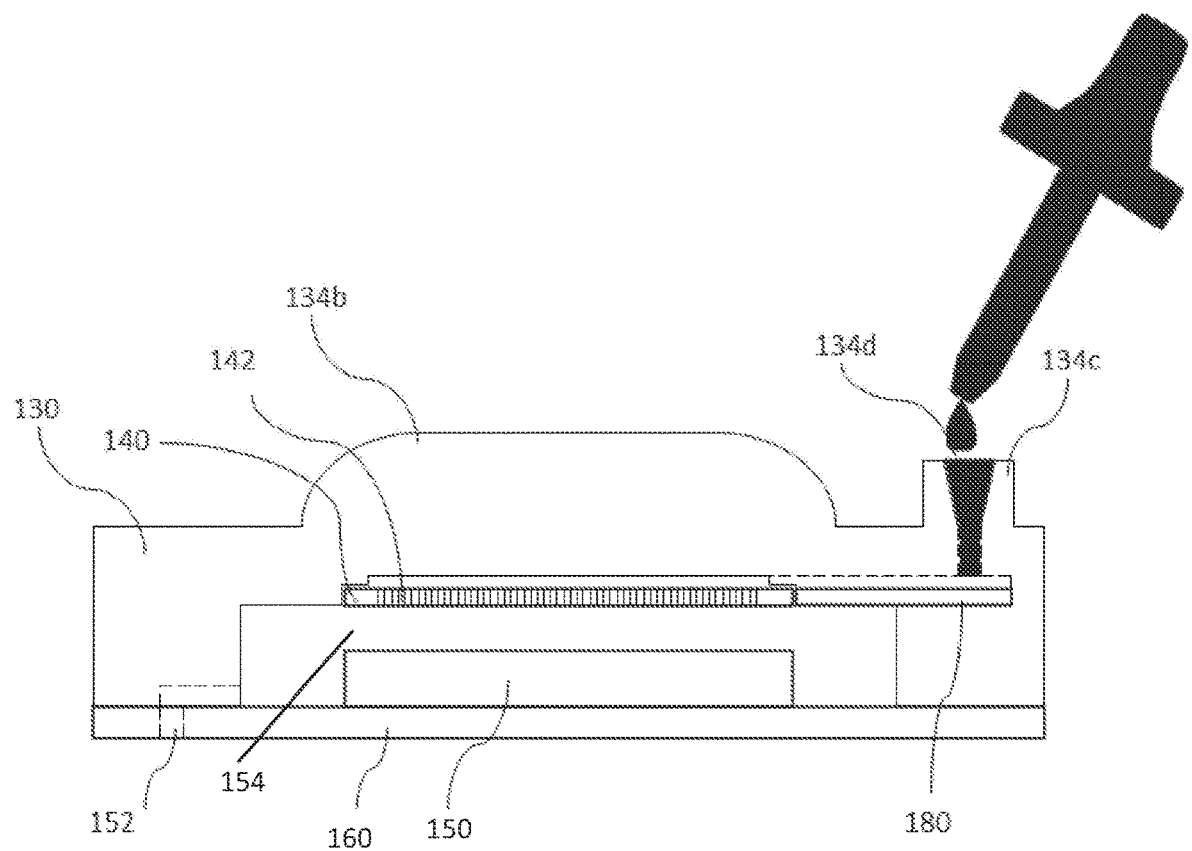
FIG. 9 is a cross-sectional view schematically illustrating a second step of the PCR process using the PCR module shown in FIG. 6.
Figure 10:
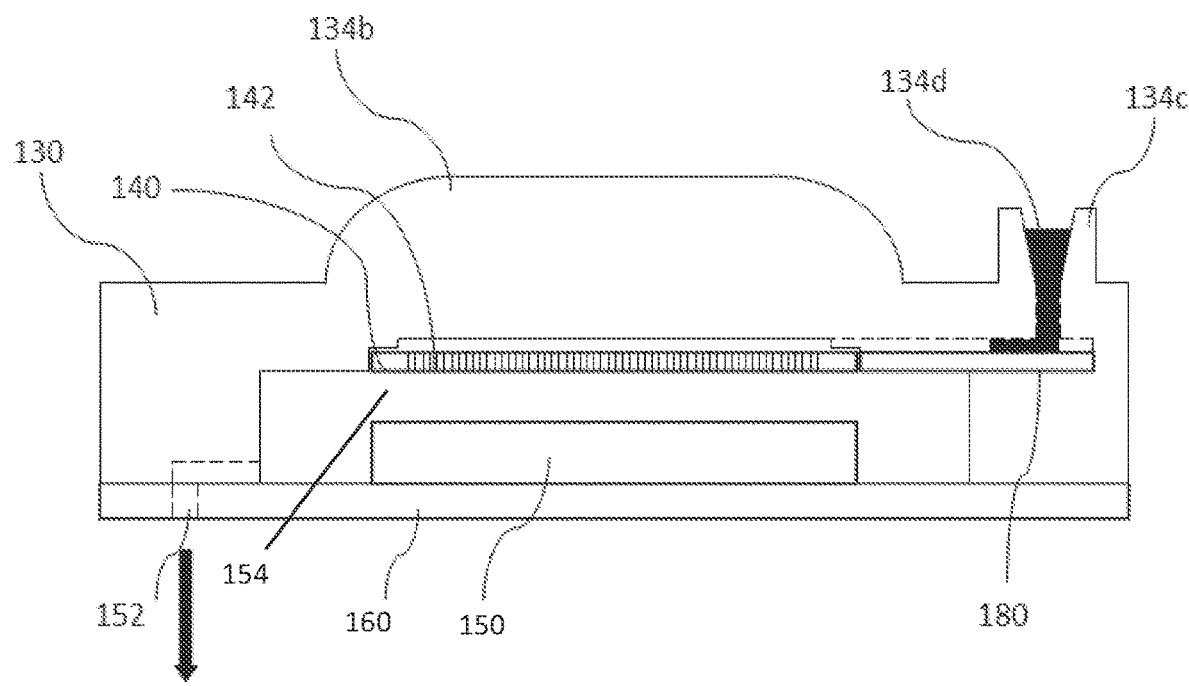
FIG. 10, FIG. 11, FIG. 12 and FIG. 13 are cross-sectional views schematically explaining a third step of the PCR process using the PCR module shown in FIG. 6.
Figure 11:
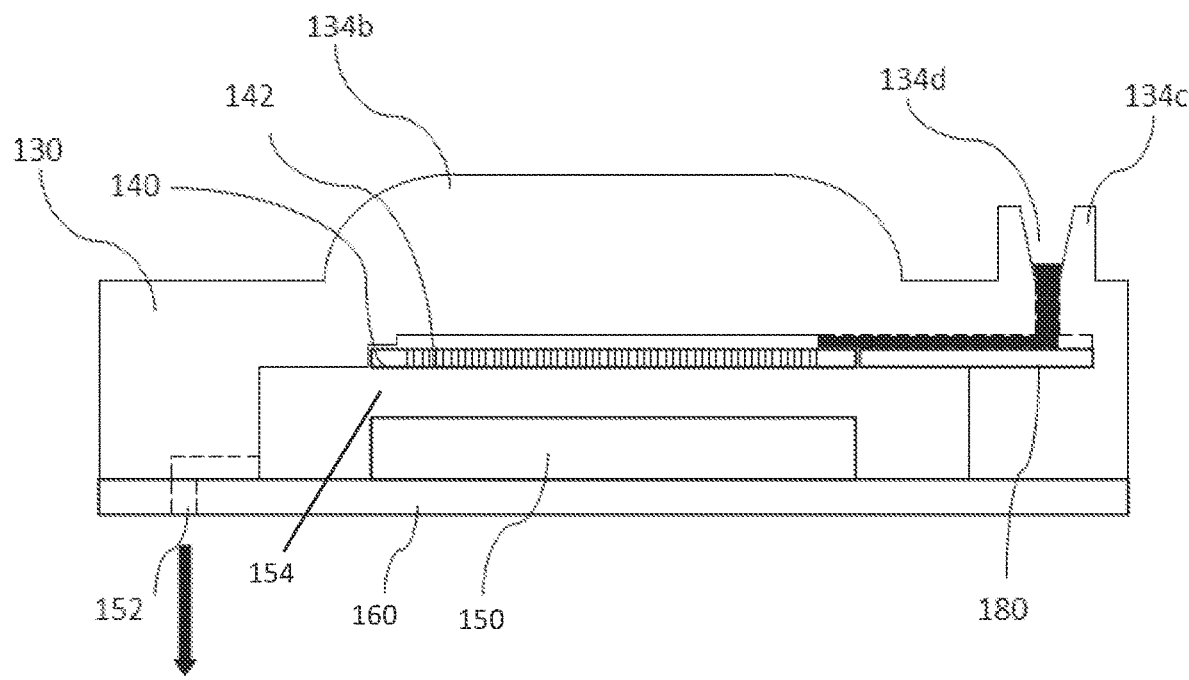
Figure 12:
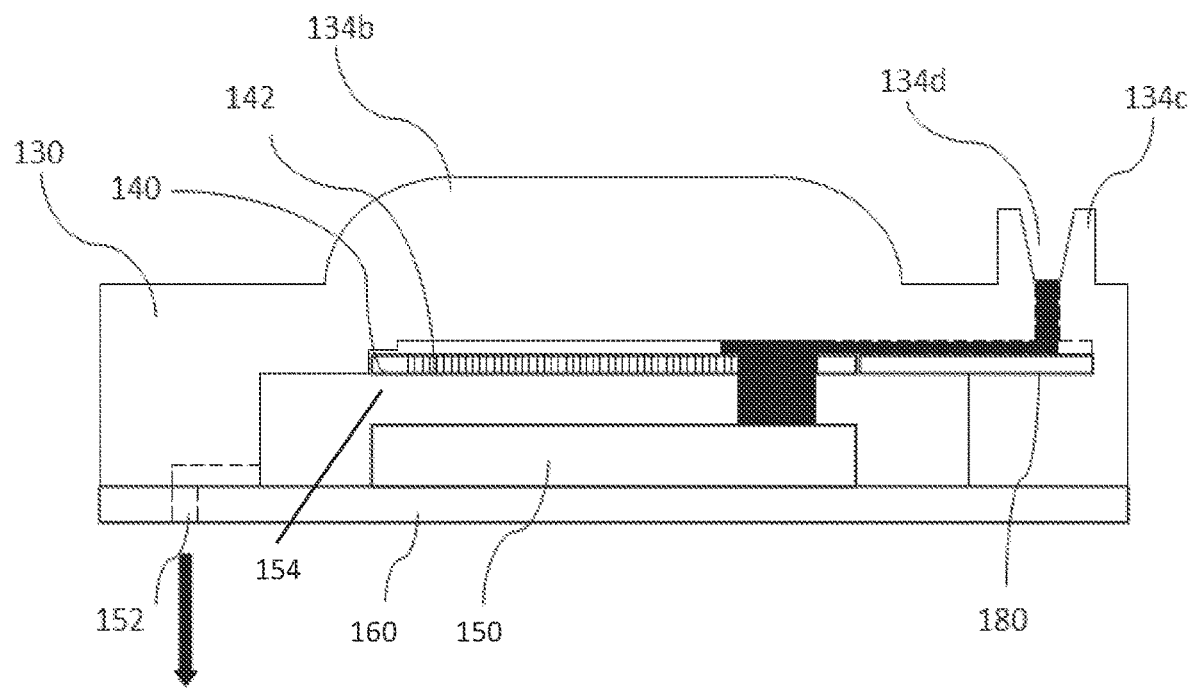
Figure 13:
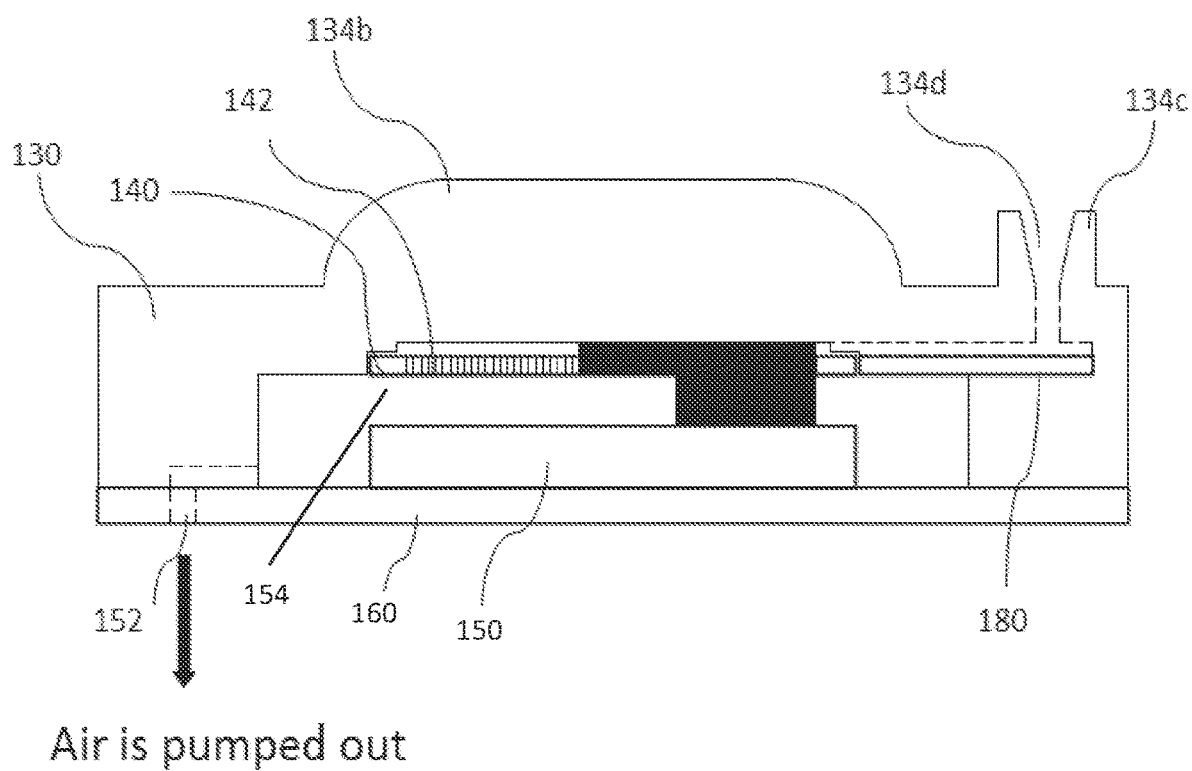

FIG. 9 is a cross-sectional view schematically illustrating a second step of the PCR process using the PCR module shown in FIG. 6.

Referring to FIG. 9, as a second step of the PCR process, liquid samples are pipetted into the inlet 134d of the microfluidic chamber 130. The amount of the liquid samples pipetted into the inlet 134d is preferably the amount that can be filled in the space between the well array 140 and the microfluidic chamber 130 and the microwells 142 of the well array 140. The liquid samples pipetted into the inlet 134d do not flow into the micro flow path 134e due to a resistance of air present in the micro flow path 134e (shown in FIG. 5B).

FIG. 10, FIG. 11, FIG. 12 and FIG. 13 are cross-sectional views schematically explaining a third step of the PCR process using the PCR module shown in FIG. 6.

Referring to FIG. 10, FIG. 11, FIG. 12 and FIG. 13, as a third step of the PCR process, liquid samples are pipetted into the inlet 134e, and then a vacuum device (not shown) connected to the vent hole 152 is turned on.

Thus, air is pumped through the vent hole 152 and a liquid sample pipetted into the inlet 134e is provided to the well array 140 along the micro flow path 134e. The liquid sample provided in the well array 140 reaches an upper portion of the CMOS photo sensor array 150 through the microwells 142 near an end of the micro flow path 134e. This pumping of the vacuum device allows the liquid sample to be provided to the microwells more quickly. Moreover, pumping of the vacuum device may more easily remove air that may be at corners or edge regions of the well array.

Figure 14:
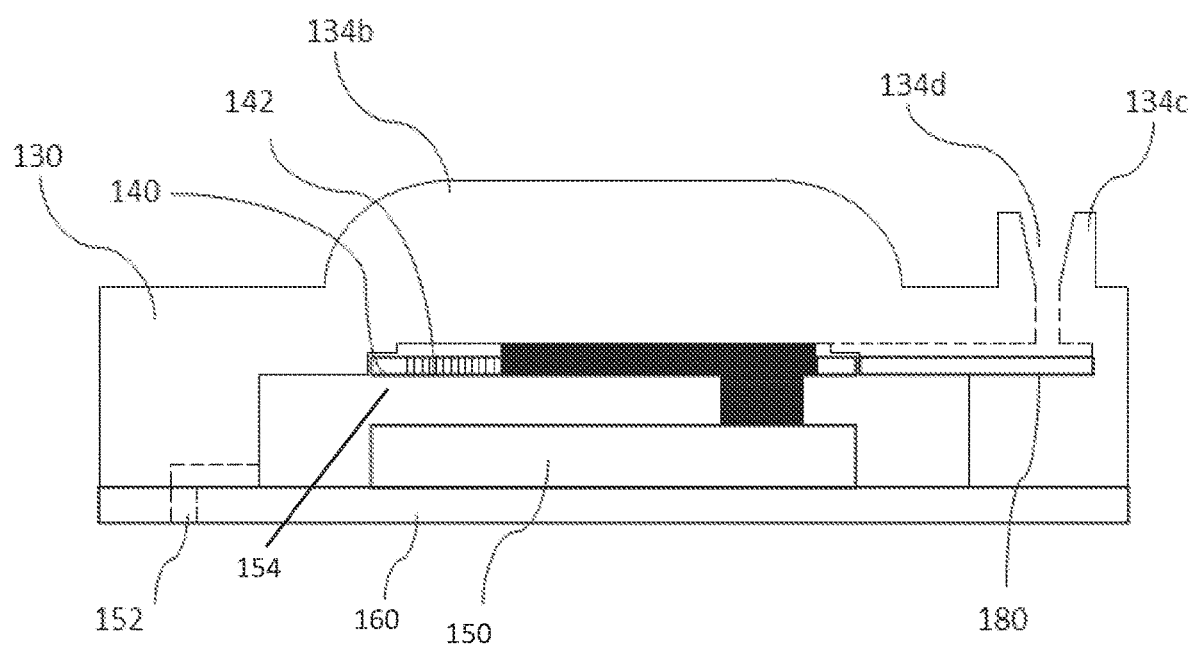
FIG. 14, FIG. 15 and FIG. 16 are cross-sectional views schematically explaining a fourth step of the PCR process using the PCR module shown in FIG. 6.
Figure 15:
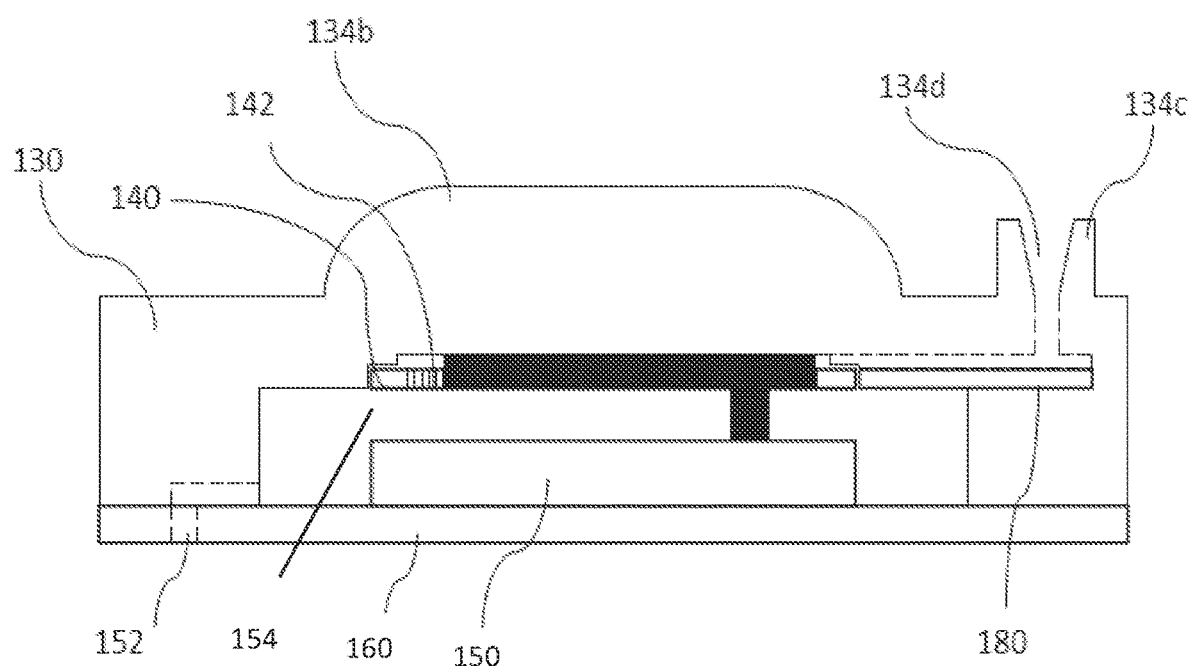
Figure 16:
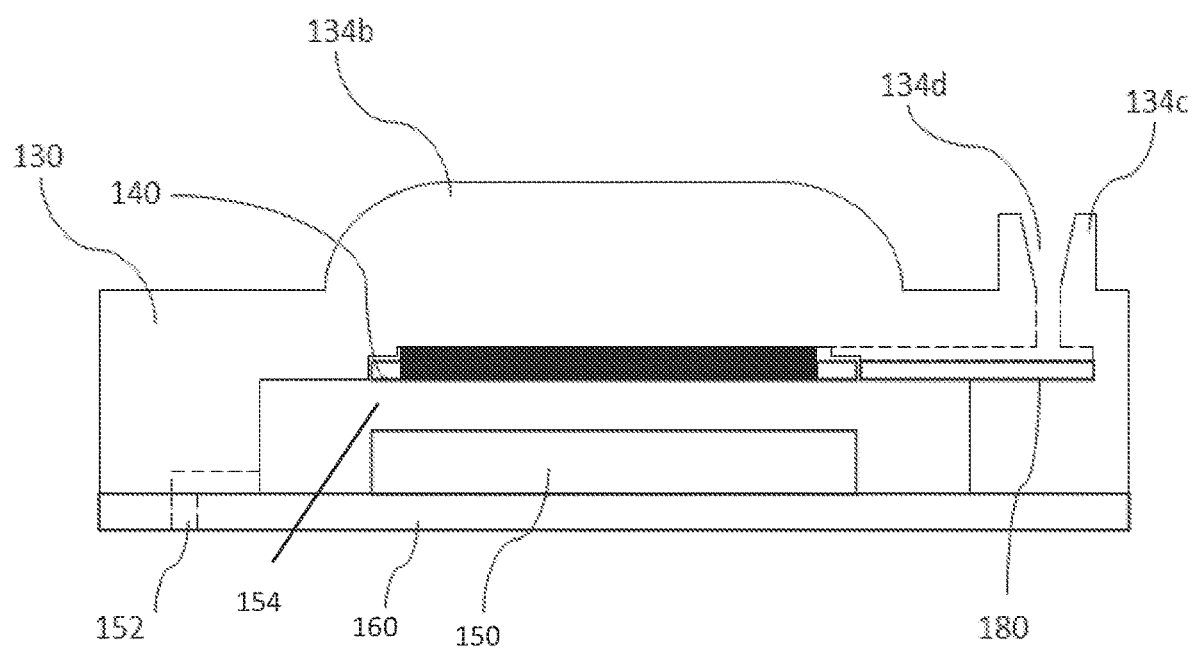
Figure 17:
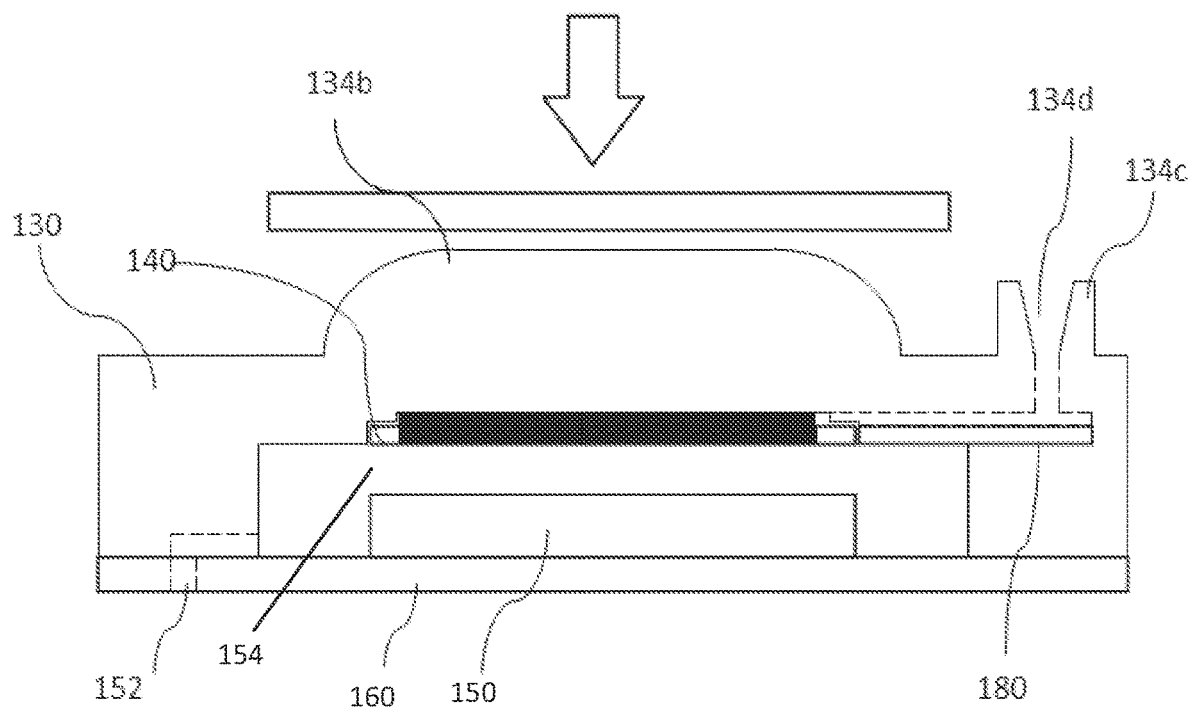
FIG. 17, FIG. 18, FIG. 19, FIG. 20 and FIG. 21 are cross-sectional views schematically explaining a fifth step of the PCR process using the PCR module shown in FIG. 6.
Figure 18:
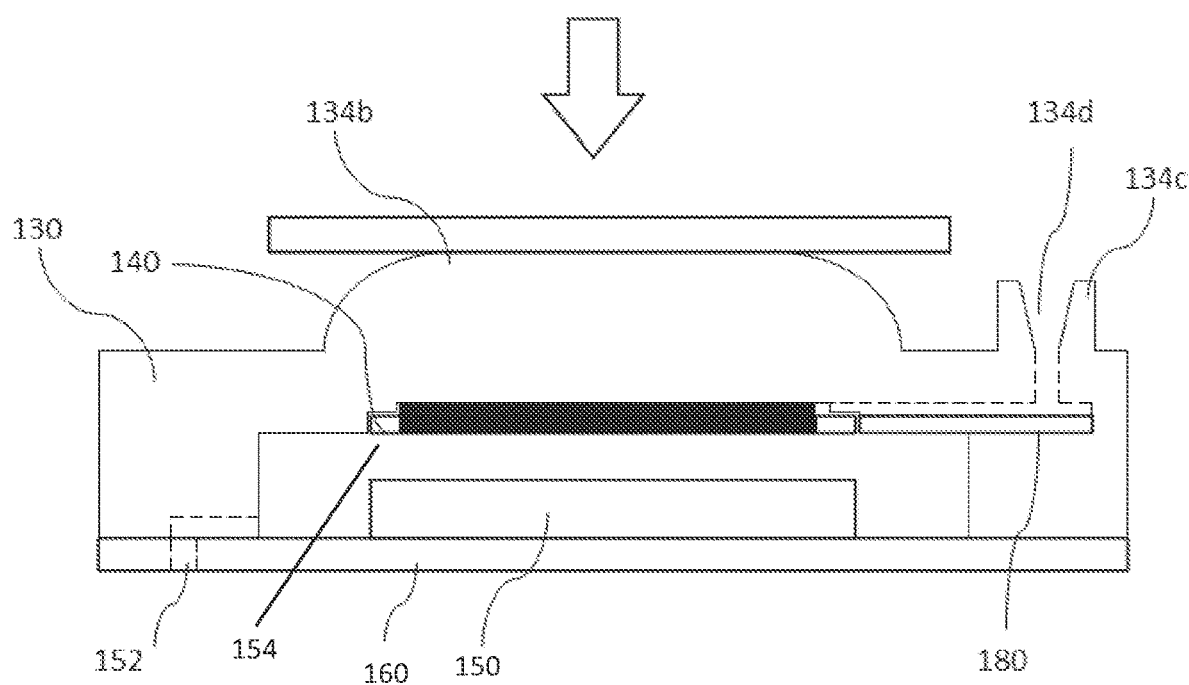
Figure 19:
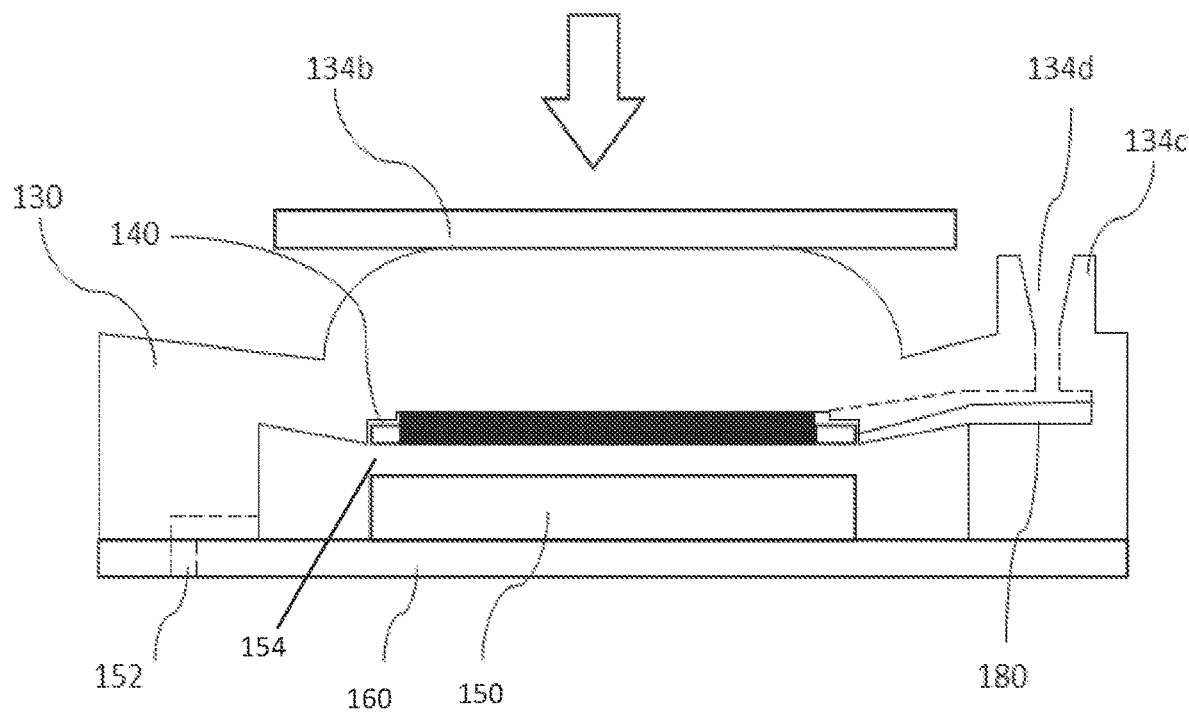
Figure 20:
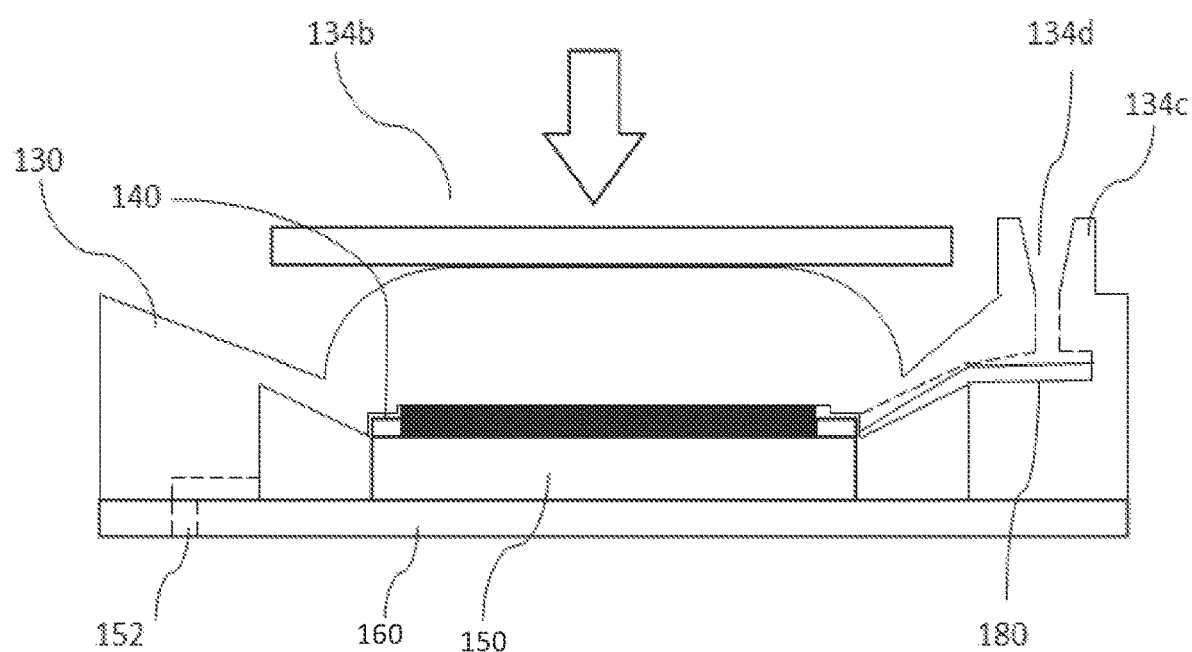
Figure 21:
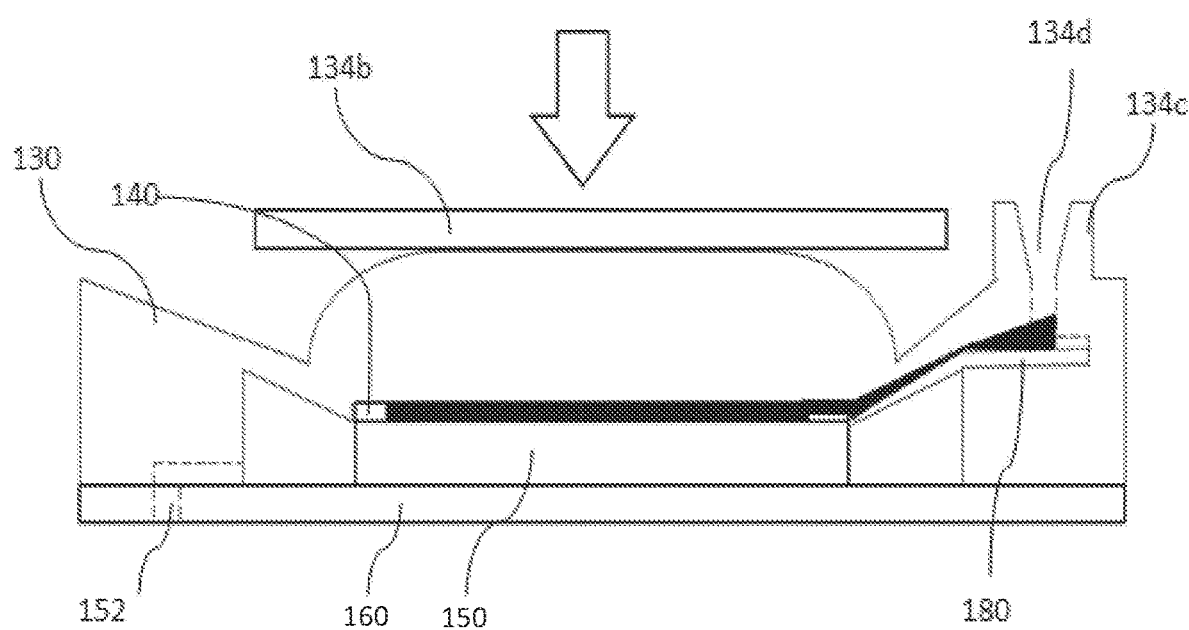

FIG. 14, FIG. 15 and FIG. 16 are cross-sectional views schematically explaining a fourth step of the PCR process using the PCR module shown in FIG. 6.

Referring to FIG. 14, FIG. 15 and FIG. 16, as a fourth step of the PCR process, the vacuum device connected to the vent hole 152 is turned off. As the vacuum device is turned off, the liquid samples reaching the lower space of the well array 140 is gradually drawn up to the upper space of the well array 140 by the capillary force.

Thus, the liquid sample is filled in the space between the well array 140 and the microfluidic chamber 130 and the microwells 142 of the well array 140.

FIG. 17, FIG. 18, FIG. 19 FIG. 20 and FIG. 21 are cross-sectional views schematically explaining a fifth step of the PCR process using the PCR module shown in FIG. 6. Particularly, the PCR process according to the sealing is shown.

Referring to FIG. 17, FIG. 18, FIG. 19, FIG. 20 and FIG. 21, as a fifth step of the PCR process, when a window member disposed in the central region of the upper case 110 is pressed in response to the user's pressing or pressurizing of the machinery, a well array 140 having a liquid sample filled in each of the wells 142 is pressed into the CMOS photo sensor array 150.

Thus, it is possible to prevent air pockets from being generated in corners or edge regions of the well array 140. The air pocket expands or shrinks due to a temperature change during the PCR process, thereby causing an error in the test result. However, according to the present invention, when the PCR solution is moved through the pumping of the vacuum device and the PCR solution fills the reaction space, a generation of air pockets in the corners and edge regions of the well array, which is the reaction space, so that it is possible to prevent an error from occurring in the test result of the air pocket in the PCR test result. Moreover, Real-time PCR reactions may also be measured because the well array is located on the CMOS photosensor array.

As described above, according to the present invention, there is no need for a separate procedure for setting the reagent since the reagent is released in the well array of the PCR module. Moreover, the possibility of contamination may be drastically degraded, and there is no need for a separate procedure for preparing the test.

In the case of digital real-time PCR, it is possible to inject a sample into each of the reaction spaces even if the size of the microwells of the well array as the reaction space is very small and the number of the reaction space is very large.

Furthermore, since the sample is injected to the corners and edge regions of the well array, air pockets may be prevented from being generated in the corners and edge regions of the well array, which is the reaction space, and the reliability of the test results may be improved.

The present invention has industrial applicability that may be used for research, disaster prevention, medical use, animal husbandry, pet treatment, and the like by an apparatus for performing biochemical inspection, a blood test apparatus, and a disease test apparatus.

Having described exemplary embodiments of the present invention, it is further noted that it is readily apparent to those of reasonable skill in the art that various modifications may be made without departing from the spirit and scope of the invention which is defined by the metes and bounds of the appended claims.

What is claimed is:

1. A cartridge for digital real-time Polymerase chain reaction (PCR) comprising:
   a microfluidic chamber including an inlet formed for injection of a liquid sample, the microfluidic chamber capable of being produced using injection molding as a fabrication technique;
   a well array including microwells through which upper and lower portions are perforated, the well array being attached to a lower surface of the microfluidic chamber;
   a CMOS photo sensor array disposed below the well array;
   a compressible space between the well array and the CMOS photo sensor array, the compressible space being uncompressed in a first state;
   a printed circuit board (PCB) having a vent that is, during the first state, in fluid communication with the compressible space, the microwells of the well array, the microfluidic chamber, and the inlet, such that the liquid sample may be received through the inlet, the microfluidic chamber, into the microwells of the well array, the compressible space and the vent by vacuum force applied to the vent;
   an upper case disposed above the microfluidic chamber and having a hole formed to correspond to the inlet;
   a bottom case coupled to the upper case to receive the microfluidic chamber, the well array, the CMOS photo sensor array, and the PCB, and having a hole corresponding to the vent; and
   a heater for thermal cycling disposed below the bottom case,
   wherein the well array including the liquid sample filled in the microwells is pressed against the CMOS photo sensor array during a second state thereby compressing the compressible space.

2. The cartridge for digital real-time PCR of claim 1, wherein the microfluidic chamber comprises:
   a base member including a first flat portion in a rectangular shape, a square support hole formed in a central region of the first flat portion, and a circular hole formed in an edge region of the first flat portion; and a top plate member including a square flat second flat plate, a dish-shaped membrane switch, and a perforated inlet, the top plate member disposed on the base member.

3. The cartridge for digital real-time PCR of claim 1, wherein the microfluidic chamber comprises at least one of a PDMS material, a transparent plastic having flexibility or transparent rubber having flexibility.

4. The cartridge for digital real-time PCR of claim 1, further comprising a sticker attached to the microfluidic chamber to form a bottom of a micro flow path formed in the microfluidic chamber.

5. The cartridge for digital real-time PCR of claim 1, wherein the well array includes at least one of etched silicon, metal, ceramic, plastic, epoxy, and photoresist resin.

6. The cartridge for digital real-time PCR of claim 1, wherein an upper surface of the CMOS photo sensor array is coated with a layer of material to form a bottom of the microwell in the second state.

7. The cartridge for digital real-time PCR of claim 6, wherein the layer of material comprises at least one of a PDMS material, a transparent plastic having flexibility or transparent rubber having flexibility.

8. The cartridge for digital real-time PCR of claim 1, wherein the well array is coated by a hydrophilic coating layer.

9. The cartridge for digital real-time PCR of claim 1, wherein the well array is attached to the microfluidic chamber by plasma or thermal or UV curing adhesive.

10. The cartridge for digital real-time PCR of claim 1, wherein the well array has a thickness of less than 700 µm.

11. The cartridge for digital real-time PCR of claim 1, wherein the microwell has a hexagonal shape, and the pitch of the microwells is less than 150 µm.

12. The cartridge for digital real-time PCR of claim 1, further comprising a window member disposed over the membrane switch,
wherein the window member is arranged corresponding to a hole formed in a central region of the upper case.

13. The cartridge for digital real-time PCR of claim 12, wherein the window member comprises a transparent material.

14. The cartridge for digital real-time PCR of claim 12, wherein the window member comprises a PDMS material.

* * * * *